United States Patent
Clemmons et al.

(10) Patent No.: US 9,851,255 B2
(45) Date of Patent: Dec. 26, 2017

(54) WINDOWLESS MICROBOLOMETER ARRAY

(71) Applicant: The Aerospace Corporation, El Segundo, CA (US)

(72) Inventors: James Hart Clemmons, Torrance, CA (US); Brian Blaise Brady, Seal Beach, CA (US); Jeffrey Louis Hall, Torrance, CA (US); Thomas Jay Curtiss, San Pedro, CA (US)

(73) Assignee: The Aerospace Corporation, El Segundo, CA (US)

( * ) Notice: Subject to any disclaimer, the term of this patent is extended or adjusted under 35 U.S.C. 154(b) by 274 days.

(21) Appl. No.: 14/736,828

(22) Filed: Jun. 11, 2015

(65) Prior Publication Data

US 2016/0363529 A1 Dec. 15, 2016

(51) Int. Cl.
*G01J 5/08* (2006.01)
*G01J 5/20* (2006.01)
*G01J 5/00* (2006.01)
*G01N 9/32* (2006.01)

(52) U.S. Cl.
CPC ............. *G01J 5/08* (2013.01); *G01J 5/0014* (2013.01); *G01J 5/0831* (2013.01); *G01J 5/0834* (2013.01); *G01J 5/20* (2013.01); *G01J 2005/0077* (2013.01); *G01N 9/32* (2013.01)

(58) Field of Classification Search
CPC ........................................................ G01J 5/08
See application file for complete search history.

(56) References Cited

U.S. PATENT DOCUMENTS

| | | |
|---|---|---|
| 7,119,337 B1 | 10/2006 | Johnson et al. |
| 7,157,711 B1 | 1/2007 | Russell |
| 7,511,274 B2 | 3/2009 | Johnson et al. |
| 7,605,370 B2 | 10/2009 | Russell |
| 7,687,776 B2 | 3/2010 | Baliga et al. |
| 7,718,965 B1 | 5/2010 | Syllaios et al. |
| 7,956,326 B1 | 6/2011 | Kychakoff et al. |
| 7,968,848 B2 | 6/2011 | Johnson et al. |
| 8,058,615 B2 | 11/2011 | McCaffrey et al. |
| 8,797,550 B2 | 8/2014 | Hays et al. |
| 2003/0208133 A1 | 11/2003 | Mault |
| 2007/0164221 A1 | 7/2007 | Russell |
| 2007/0221848 A1 | 9/2007 | Johnson et al. |
| 2008/0251724 A1 | 10/2008 | Baliga et al. |

(Continued)

OTHER PUBLICATIONS

Aamer Mahmood et al., "Micromachined bolometers on polyimide", published on www.sciencedirect.com and available on Apr. 18, 2006.

(Continued)

*Primary Examiner* — David Porta
*Assistant Examiner* — Hugh H Maupin
(74) *Attorney, Agent, or Firm* — LeonardPatel PC (57) ABSTRACT

A windowless microbolometer for use in terrestrial applications and non-terrestrial applications is provided. The windowless microbolometer array may interact with a flow of gas such that a pixel-based image of the gas is generated when the flow of gas impinges upon the windowless microbolometer array. The windowless microbolometer array may also interact with a molecular beam to provide information related to density, shape, and propagation of the molecular beam.

23 Claims, 11 Drawing Sheets

(56) References Cited

U.S. PATENT DOCUMENTS

| | | | |
|---|---|---|---|
| 2009/0218493 | A1 | 9/2009 | McCaffrey et al. |
| 2010/0006761 | A1 | 1/2010 | Johnson et al. |
| 2010/0133536 | A1 | 6/2010 | Syllaios et al. |
| 2012/0049068 | A1 | 3/2012 | McCaffrey et al. |
| 2012/0050750 | A1 | 3/2012 | Hays et al. |
| 2012/0101747 | A1 | 4/2012 | Kielkopf et al. |
| 2012/0181431 | A1 | 7/2012 | Mitin et al. |
| 2012/0293192 | A1* | 11/2012 | Lapington ............. G01T 1/2935 324/691 |
| 2012/0326047 | A1* | 12/2012 | Kennedy ................... G01T 3/04 250/390.01 |
| 2014/0168433 | A1 | 6/2014 | Frank et al. |
| 2014/0247323 | A1* | 9/2014 | Griffis ................ H04N 5/23238 348/36 |
| 2014/0267756 | A1 | 9/2014 | Gousev et al. |

OTHER PUBLICATIONS

CEDIP Infrared Systems, "Infrared Gas Imaging. A new industrial solution for live imaging and concentration measurement of gases.", published on www.cedip.infrared.com, first viewed on Jan. 9, 2015.
E.Punce et al., "Transient Luminuos Events observed by a pinhole camera", published 33rd International Cosmic Ray Conference, Rio De Janeiro, Jan. 2013.

* cited by examiner

WINDOWLESS MICROBOLOMETER ARRAY

FIELD

The present invention relates to a windowless microbolometer array, and in particular, to a windowless microbolometer array configured for imaging.

BACKGROUND

Measurements of upper atmosphere characteristics may include gas density, gas temperature, wind direction, and wind magnitude. Generally, there are two techniques used to make measurements or estimates for each of these parameters. The first technique is remote sensing that senses these parameters from a distance. The second technique is in-situ sensing that senses these parameters locally.

A variety of remote sensing methods currently exist. One class of methods registers signals from naturally existing airflow by use of sensitive optical components in space or on the ground. These methods integrate over a large volume of space, which suppresses detection of highly-structured atmospheric components. Another class of remote sensing methods is LIDAR-based sensing. LIDAR-based sensing utilizes active probing with an intense light source and performs a measurement of the signal returned by the atmosphere. These methods generally have been limited to altitudes below ~150 km.

In situ techniques that make local measurements have also been used, and these methods generally detect gas directly on space-based platforms. Sensors based on pressure gauges or mass spectrometers have been used to make density measurements. Wind measurements have been made by sensors that modulate the flow of gas into the sensor by use of moving mechanical baffles, or using energy analysis of gas constituents after first ionizing those constituents within the instruments.

However, both of these techniques provide significant challenges for measurement of upper atmosphere characteristics. For example, with remote sensing, sensitivity is lost because measurement is performed over a large volume of space. With in-situ sensing, a more complex gas sensor is required and ionization of gas constituents is also required.

Thus, an alternative approach for measuring upper atmosphere gas characteristics may be beneficial.

SUMMARY

Certain embodiments of the present invention may provide solutions to the problems and needs in the art that have not yet been fully identified, appreciated, or solved by current upper atmosphere gas sensors. For example, in some embodiments, an upper atmosphere gas sensor (or an apparatus) may be used for measurement of upper atmosphere characteristics such as gas density, gas temperature, and winds.

In one embodiment, an apparatus includes a windowless microbolometer array that interacts with a flow of gas such that a pixel-based image of the gas is generated when the flow of gas impinges upon the windowless microbolometer array.

In another embodiment, an apparatus includes an aperture that admits a flow of gas into a housing allowing the gas to impinge on the windowless microbolometer array. The apparatus also includes a computing system that generates a pixel-based image of the gas when the gas impinges on the windowless microbolometer array.

In yet another embodiment, an apparatus includes a windowless microbolometer array configured to interact with a molecular beam to provide information related to density, shape, and propagation of the molecular beam.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments of the present invention pertain to an upper atmosphere gas sensor (hereinafter "sensor") that may be used at altitudes of approximately 80 kilometers, and be configured to measure properties of the gas (e.g., density, temperature, wind vectors, and composition). In some embodiments, 80 kilometers may be the lower limit of the altitude range of applicability while the upper limit is dependent on the signal strength due to decreasing gas density. The sensor may be located, for example, on a vehicle, such as an orbiting platform or a suborbital space vehicle moving at high speeds through the upper atmosphere. In such an embodiment, the high speed moving vehicle may operate at speeds greater than 100 meters per second. In other embodiments, the sensor may be located on a stationary vehicle or a slow moving vehicle to measure, for example, the characteristics of the molecular beam.

The sensor may include a housing that surrounds a windowless microbolometer array. The housing may include an aperture that admits gas into the housing. The housing may create a gas plume that strikes the windowless microbolometer array. As the gas plume strikes the windowless microbolometer array, a pixel-based image of the gas may be generated by an electronic readout and data processing system (hereinafter "computing system"). The pixel-based image of the gas may be created based on the energy of the gas deposited on the windowless microbolometer array. The pixel-based image (or resulting pattern) may provide information about the gas density, the gas temperature, and the wind vector of the admitted gas. The wind vector may be determined by the location at which the gas impinged on the windowless microbolometer array. If the generated image is large, the gas in the upper atmosphere is relatively warm and, conversely, if the generated image is small, the gas in the upper atmosphere is relatively cool. Similarly, if the gas is dense, a brighter image is generated and, conversely, if the gas is less dense, a dimmer image is generated.

Figure 1A:
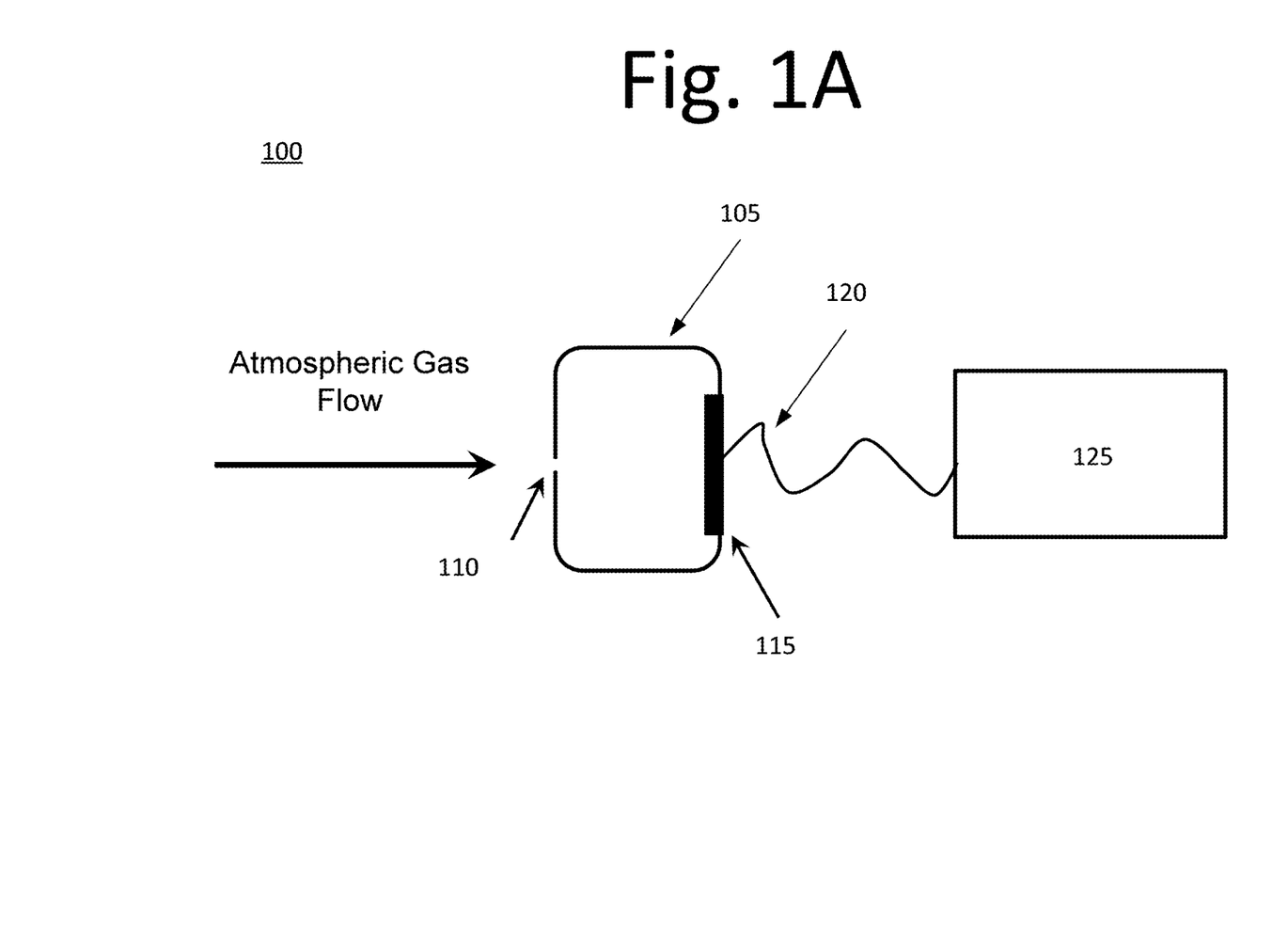
FIGS. 1A-1C illustrate an upper atmosphere gas sensor, according to an embodiment of the present invention.
Figure 1B:
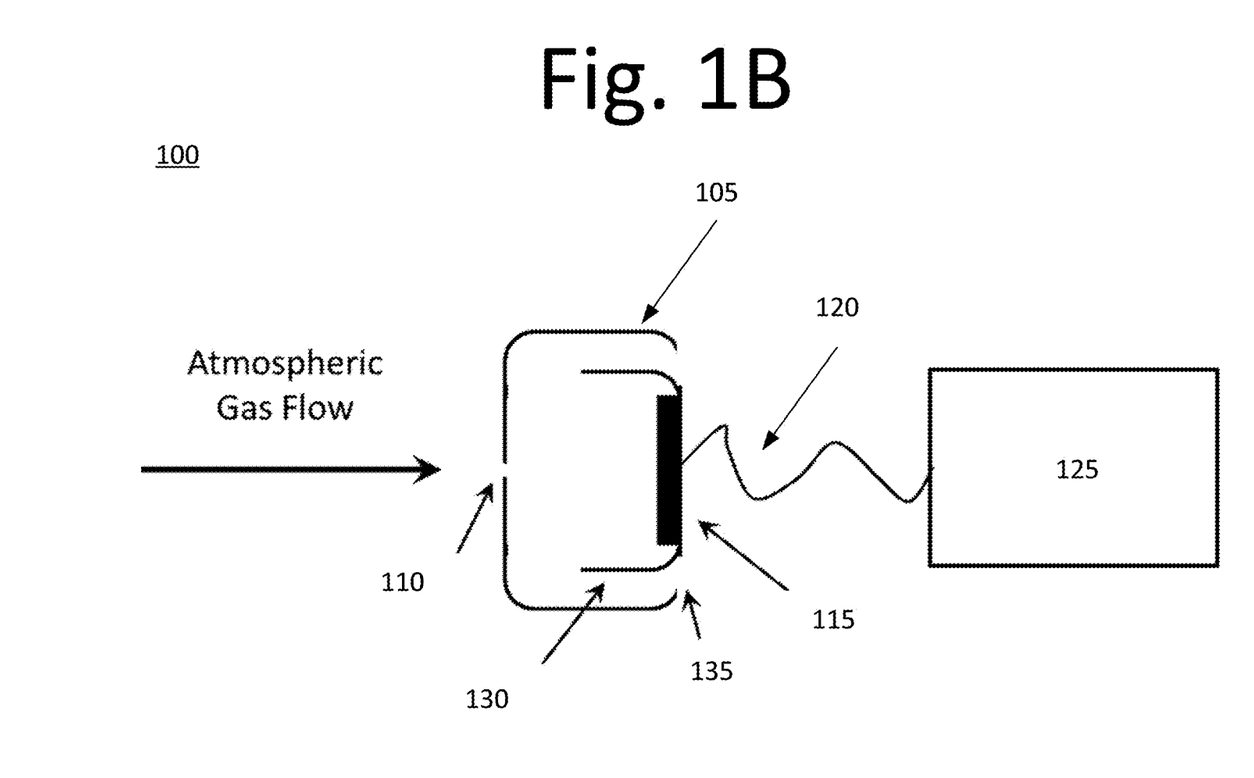
Figure 1C:
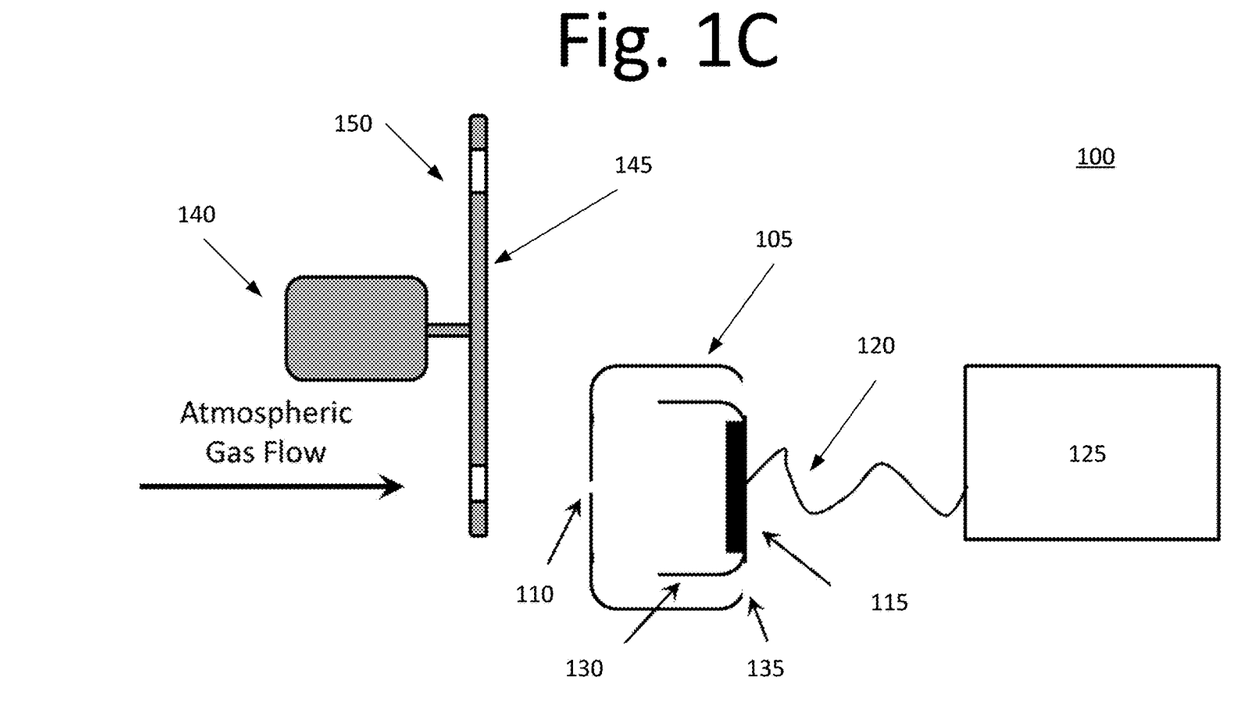

FIGS. 1A-1C illustrate a sensor 100, according to an embodiment of the present invention. As mentioned above, sensor 100 may be located on a vehicle (not shown) in the upper atmosphere. In certain embodiments, sensor 100 may be operated in any rarefied atmosphere. In a further embodiment, sensor 100 may be used within the atmospheres of other planetary bodies in regions where the atmosphere is not too thick and not too tenuous.

In this embodiment, sensor 100 includes a housing 105. Housing 105 may be made of metal, aluminum, or any type of material suitable for holding atmospheric gas. A flow of atmospheric gas is admitted into housing 105 through an aperture 110. The size and shape of aperture may vary depending on the embodiment. In some embodiments, depending on the direction of the wind and/or the movement of the vehicle, the flow of atmospheric gas may be admitted through aperture 110 at an angle (i.e., not horizontal).

As the flow of gas is admitted into housing 105, the wind and/or the motion of the vehicle causes the gas to impinge on windowless microbolometer array 115. In this embodiment, information from the gas impingement is transmitted from windowless microbolometer array 115 to a computing system 125 via a signal cable 120. For instance, transmitted information may include temperature of each pixel in windowless microbolometer array 115. The temperature of each pixel shows a measurement of the amount of energy transmitted from the flow of gas to the pixels. In other embodiments, the information may be transferred wirelessly from windowless microbolometer array 115 to computing system 125. This wireless transfer may occur via Bluetooth™ technology, WIFI technology, WIMAX technology, etc.

Computing system 125 may read and process the information to generate a pixel-based image of the gas impingement. The pixel-based image of the gas, for example, may be created based on the energy of the gas deposited on windowless microbolometer array 115. The pixel-based image (or resulting pattern) provides information about the density, temperature, and wind vector of the admitted gas. See, for example, images 200 and 300 of FIGS. 2 and 3.

Figure 2:
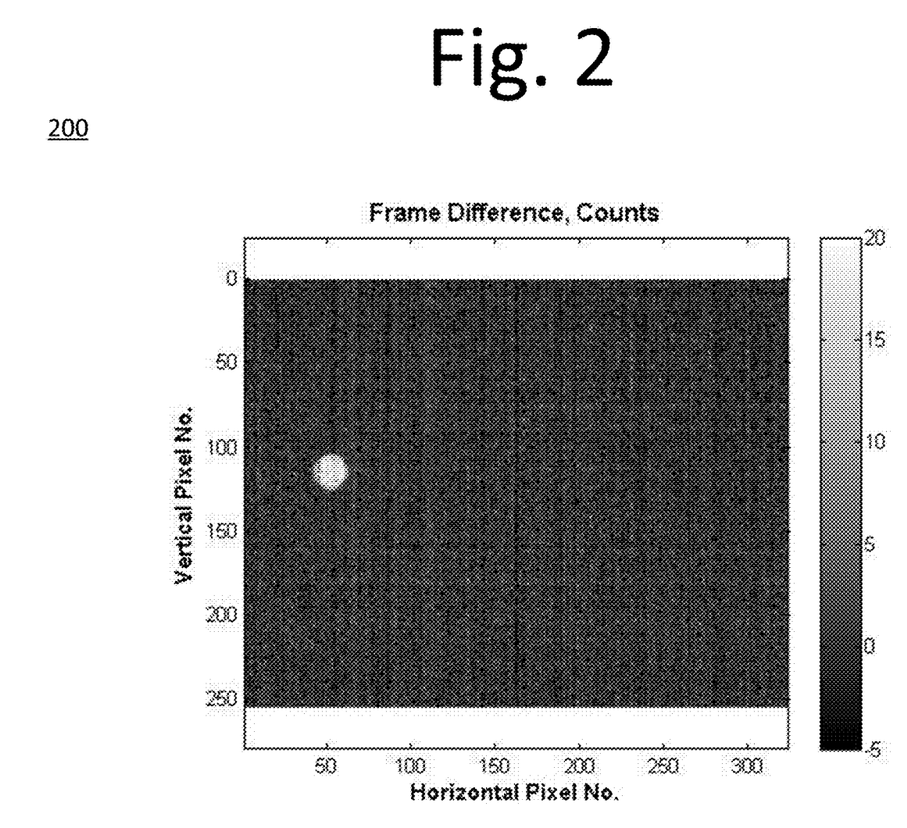
FIG. 2 is a graph illustrating an image of upper atmosphere gas simulated by a cold beam using a 500 micron aperture, according to an embodiment of the present invention

FIG. 2 is a graph 200 illustrating an image of upper atmosphere gas simulated by a cold beam using a 500 micron aperture, according to an embodiment of the present invention. In this embodiment, graph 200 shows a beam directed along aperture. The diameter of the spot on the sensor matches the aperture size because a cold beam was utilized. While this embodiment uses a 500 micron aperture, in other embodiments, the size of the aperture may vary depending on the application. For example, at relatively low altitudes, the aperture size may be smaller.

Figure 3:
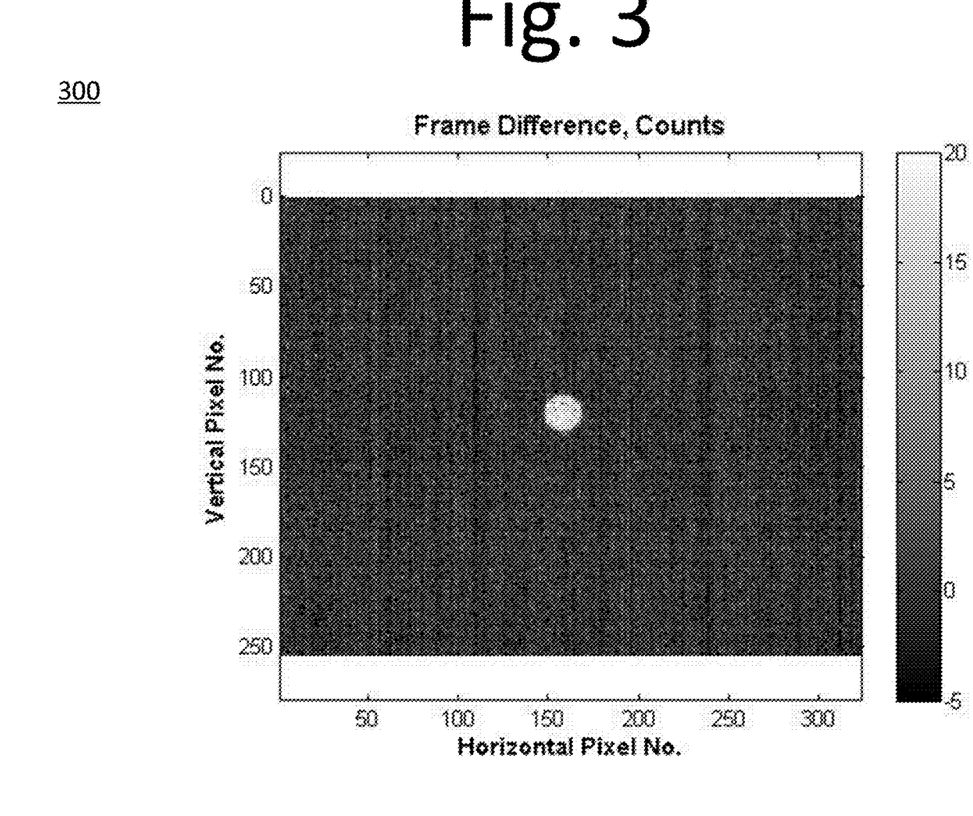
FIG. 3 is a graph illustrating another image of upper atmosphere gas simulated by a cold beam using a 500 micron aperture, according to an embodiment of the present invention.

FIG. 3 is a graph 300 illustrating an image of upper atmosphere gas simulated by a cold beam using a 500 micron aperture, according to an embodiment of the present invention. Similar to FIG. 2, the aperture size may vary depending on the embodiment. In this embodiment, graph 300 shows an image obtained with the beam directed approximately 17 degrees from the aperture. The displacement of the spot shows how the direction is imaged by the sensor.

Returning to FIG. 1, and in particular, FIG. 1B, sensor 100 may include a baffle 130 and a vent 135 to create a baffled vent in some embodiments. In those embodiments, baffled vent rapidly releases gas that has been measured to prevent interference with any new gas that will be measured. In other words, the baffled vent provides an augmented exhaust capability allowing gas, which has already deposited its flow of energy onto windowless microbolometer array 115, to quickly escape housing 105. While sensor 100 in FIG. 1B utilizes a baffled vent to create venting holes, in other embodiments, sensor 100 may include one or more holes (not shown) on each side of windowless microbolometer array 115, allowing gas to escape.

In certain embodiments, a chopper wheel 145 with at least one aperture 150 may be placed in front of sensor 100. See FIG. 1C. In this embodiment, aperture 150 of chopper wheel 145 is placed directly in front of aperture 110 of housing 105. A motor 140 may rotate or spin chopper wheel 145, allowing atmospheric gas to flow through chopper wheel 145, and in particular, to flow through apertures 150. The implementation of chopper wheel 145 in this embodiment allows measurement of velocity of the gas using a different technique, which may rely on timing. For example, through control and/or measurement, when at least one aperture 150 crosses or is directly in front of aperture 110, a puff of gas may pass through aperture 150 and aperture 110 such that the puff of gas may be detected by windowless microbolometer array 115. This allows the speed of the gas flow to be calculated since the distance between chopper wheel 145 and sensor 100 is known.

It should be appreciated that the sensor described herein provides advantages over conventional sensors. For example, the sensor uses a non-complex configuration to reduce the mass, size, and power, all of which are critical to space flight use. The sensor may be implemented on research satellites in the upper atmosphere, on sounding rocket platforms, or on a real-time atmospheric monitor for operational vehicles in low Earth orbit (LEO). The sensor may also be used, for example, in a CubeSat form factor. In such an embodiment, a plurality of CubeSats may be deployed to provide an array of upper atmosphere gas sensors. This may provide real-time awareness of the upper atmosphere, i.e., improve tracking orbiting objects and models of the Earth's upper atmosphere that are used for tracking and reentry predictions.

It should be appreciated that a windowless microbolometer array may be utilized in other applications, such molecular beam imaging. For molecular beam imaging, conventional methods first ionize a portion of the molecular beam to be imaged by an impingement of laser light or charged particles. The ions can then be detected using a microchannel-plate based imaging device. However, these methods require relatively sophisticated equipment.

Furthermore, a resulting image of the molecular beam will depend on the characteristic of the molecular beam to be imaged, the structure of the ionizing light or charged particle of the molecular beam, and the subsequent transport of the ionizing particles to the imaging device. Moreover, only a fraction of the molecular beam is actually produced as an image.

Figure 4:
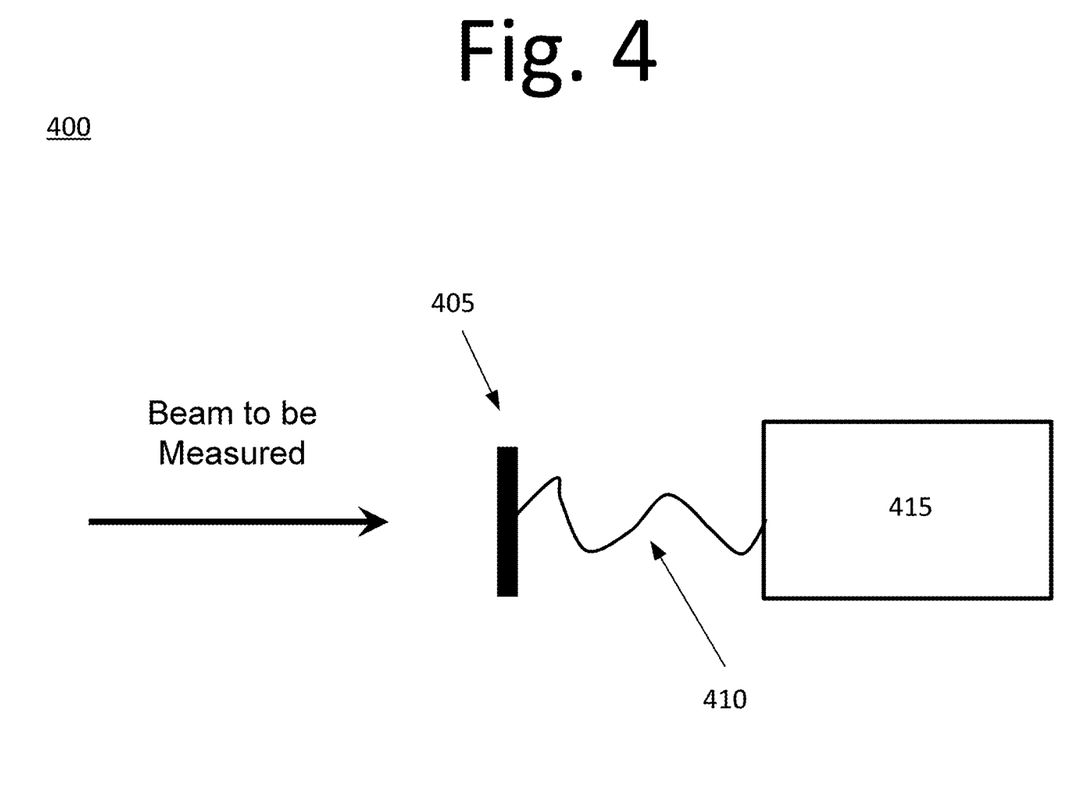
FIG. 4 illustrates a molecular beam imager, according to an embodiment of the present invention.

Thus, an alternative system for performing molecular beam imaging utilizing a windowless microbolometer array may be beneficial. FIG. 4 illustrates a molecular beam imager (hereinafter "imager") 400, according to an embodiment of the present invention. In this embodiment, a window may be removed from a microbolometer array to create a windowless microbolometer array 405. This may allow windowless microbolometer array 405 to be sensitive to all desired forms of energy.

In certain embodiments, imager 400 may be located within a vacuum chamber (not shown), allowing measurements of a molecular beam to be performed. In particular, windowless microbolometer array 405 may be located in a terrestrial or space vacuum. For example, windowless microbolometer array 405 may be placed at the terminus of the molecular beam apparatus (not shown) allowing a user to determine whether the molecular beam apparatus is operating efficiently and/or correctly.

In this embodiment, imager 400 is configured to produce a pixel-based image of the molecular beam based on energy deposited into a windowless microbolometer array 405. For example, a molecular beam that is to be measured is transmitted to a windowless microbolometer array 405. In some embodiments, windowless microbolometer array 405 may have sensitivity limits. In those embodiments, for example, windowless microbolometer array 405 may have sensitivity limits around 1e-11 W/pixel, with the pixels being approximately 17 μm on a side. In other embodiments, depending on the sensitivity, windowless microbolometer array 405 may have greater sensitivity allowing weaker beams to be imaged.

As discussed above, windowless microbolometer array 405 may be sensitive to molecules and atoms, allowing a pattern to be generated by computing system 415 when the molecular beam impinges on windowless microbolometer array 405. This pattern may provide information about the density, shape, and propagation of the molecular beam. This information may be transmitted by a signal cable 410 to computing system 415 for processing and output.

During operation, the amount of energy from the molecular beam that is deposited into each pixel of windowless microbolometer array 405 relates to the amount of energy contained in a gas parcel that impinges on that pixel. In some embodiments, gas may be admitted onto windowless microbolometer array 405 by placing windowless microbolometer array 405 in the path of the molecular beam. The position of the centroid may provide the position of the center of the molecular beam, while the extent of the image may indicate the beam width. The structure of the molecular beam is reflected in the image structure.

In some embodiments, imager 400 may include additional components such as a vacuum positioning system (not shown) and/or a set of apertures (also not shown). The vacuum positioning system may be configured to vertically and/or horizontally move imager, and possibly, to rotate imager 400 to image the molecular beams. For example, a system of motors (not shown) may be utilized in some embodiment to move and/or rotate image 400. This way, the molecular beams may impinge in a wider area and/or from a variety of directions. The set of apertures may be moved in and out of the field of view of imager 400 to provide further information as to the direction, size, and cross-sectional shape of the molecular beam.

The embodiments of imager 400 utilize a relatively simple, inexpensive setup that uses few components. Imager 400 directly detects the molecular beam rather than converting the molecular beam to ions and transporting the ions to the detector to be imaged. Finally, imager 400 utilizes the entire molecular beam to be imaged rather than a portion of the molecular beam.

Figure 5:
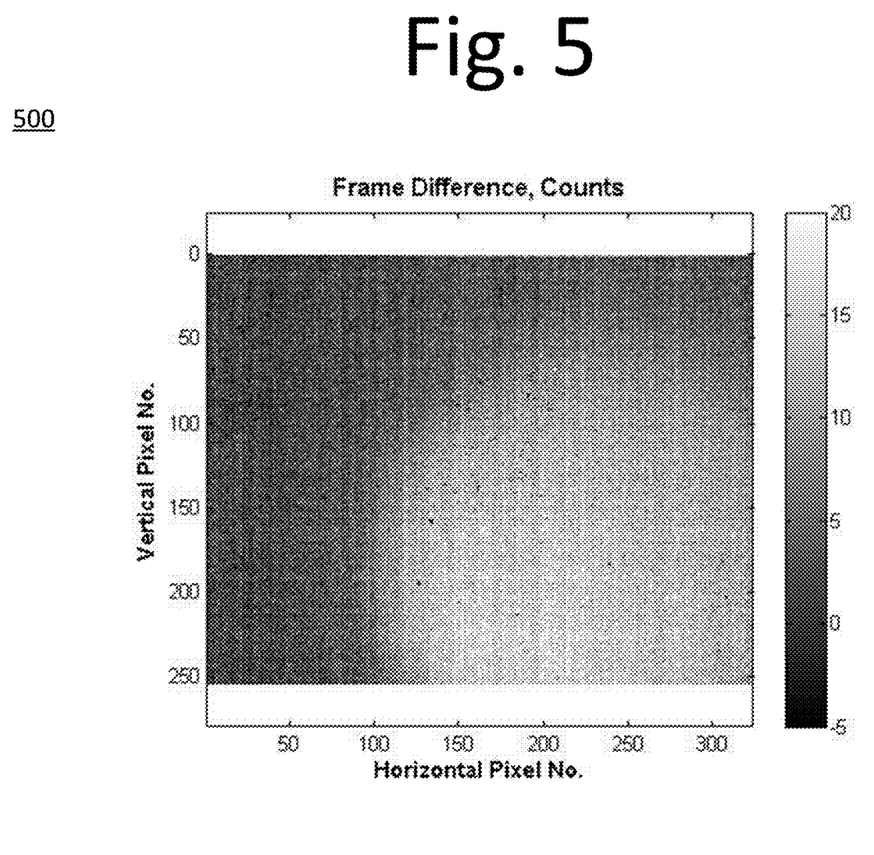
FIG. 5 is a graph illustrating a beam image, according to an embodiment of the present invention.

FIG. 5 is a graph 500 illustrating an image of a molecular beam, according to an embodiment of the present invention. In this embodiment, graph 500 shows that the molecular beam has traveled through an open ball valve before impinging on the imager. Graph 500 also shows that the molecular beam is not centered on the imager and the beam exhibited non-uniformity, possibly as a result of the interaction with the ball valve. In particular, the lighter shaded area shows where the molecular beam is impinging with relatively high intensity, and the darker shaded area shows where the molecular beam is impinging with little or no intensity.

Figure 6:
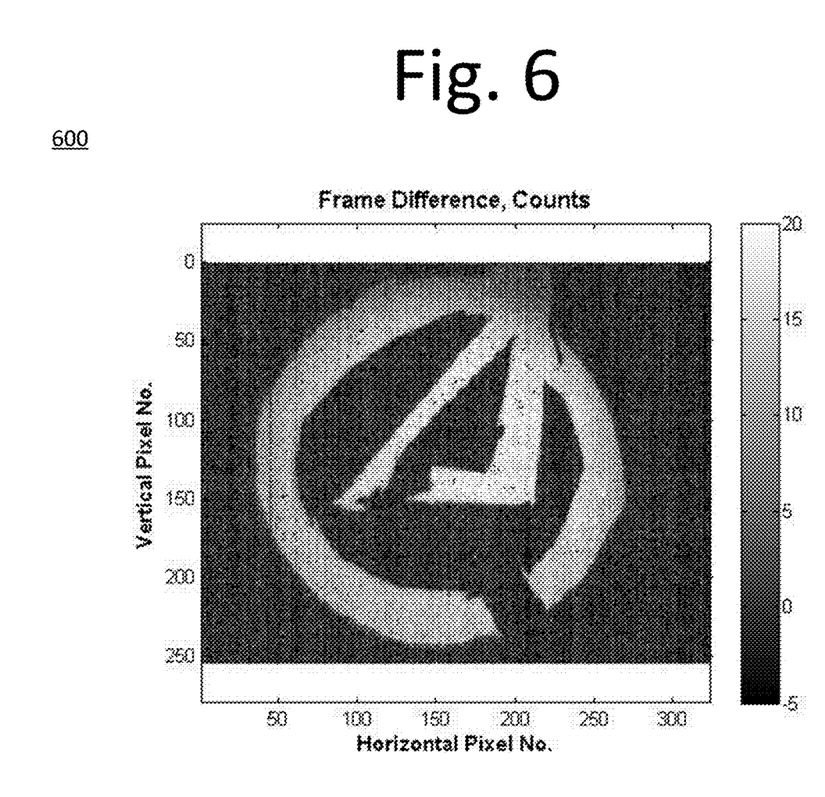
FIG. 6 is a graph illustrating a beam image, according to an embodiment of the present invention.

FIG. 6 is a graph 600 illustrating an image of a molecular beam, according to an embodiment of the present invention. In this embodiment, a mask is placed in front of the molecular beam generator. Graph 600 shows that portions of the molecular beam that traveled through the mask and impinged on the windowless microbolometer array. Similar to FIG. 5, the lighter shaded area shows where the molecular beam is impinging with relatively high intensity, and the darker shaded area shows where the molecular beam is impinging with little or no intensity.

It should be appreciated that the imager shown in FIG. 4, and explained with respect to FIGS. 5 and 6, may be utilized for applications that require knowledge of properties of the molecular beam (e.g., position, width, and intensity) within a laboratory or other vacuum facility. For instance, the imager may be used for aligning components of the molecular beam system and for understanding the position and structure of the beam. The imager may also verify that the molecular beam system is performing according to its design parameters.

Figure 7:
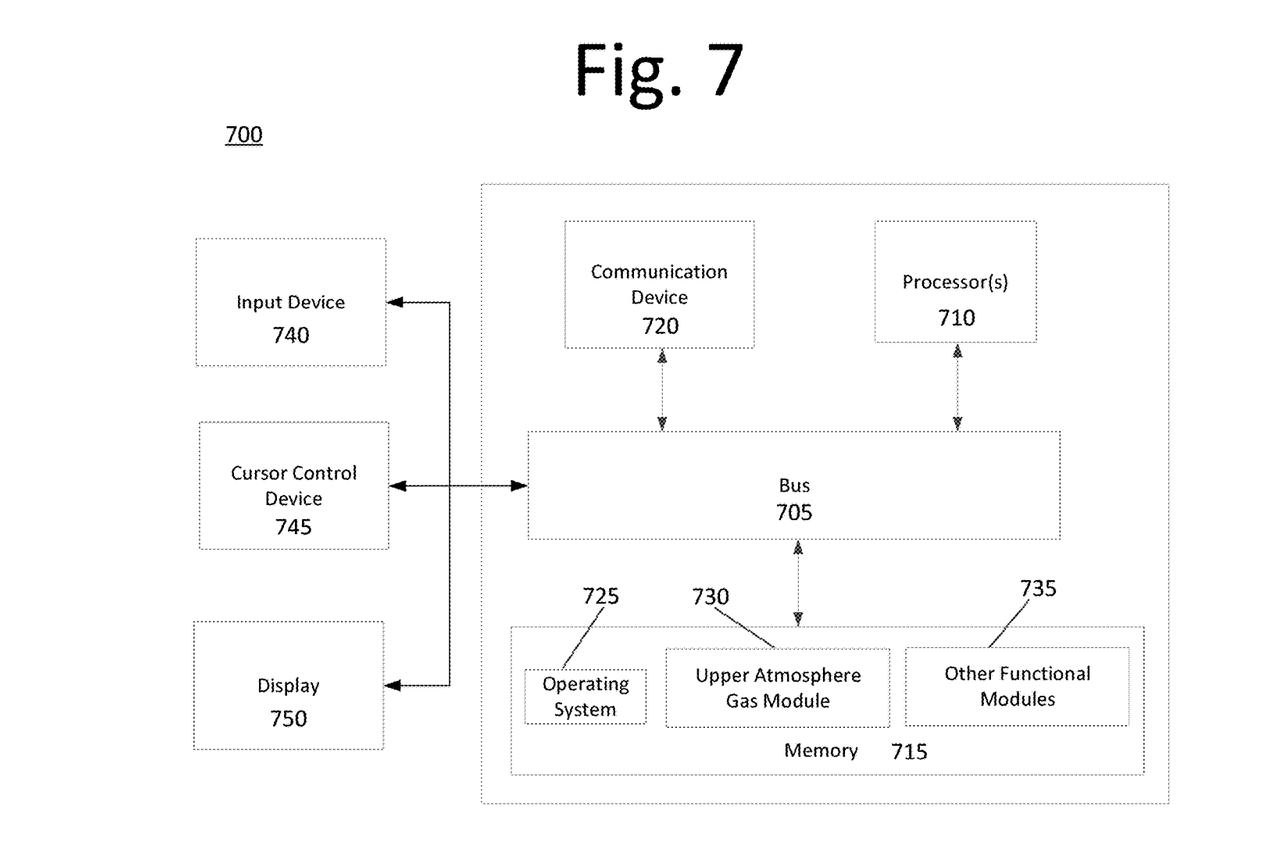
FIG. 7 is a block diagram illustrating a computing system for upper atmosphere gas sensing and molecular beam imaging, according to an embodiment of the present invention.

FIG. 7 is a block diagram illustrating a computing system 700 for an upper atmosphere gas sensing and molecular beam imaging, according to an embodiment of the present invention. Computing system 700 includes a bus 705 or other communication mechanism for communicating information, and processor(s) 710 coupled to bus 705 for processing information. Processor(s) 710 may be any type of general or specific purpose processor, including a central processing unit (CPU) or application specific integrated circuit (ASIC). System 700 further includes a memory 715 for storing information and instructions to be executed by processor(s) 710. Memory 715 can be comprised of any combination of random access memory ("RAM"), read only memory ("ROM"), flash memory, cache, static storage such as a magnetic or optical disk, or any other types of non-transitory computer-readable media or combinations thereof. Additionally, system 700 includes a communication device 720, such as a transceiver, to facilitate wired or wireless communication with a windowless microbolometer array or any other type of external system.

Non-transitory computer-readable media may be any available media that can be accessed by processor(s) 710 and may include both volatile and non-volatile media, removable and non-removable media, and communication media. Communication media may include computer-readable instructions, data structures, program modules or other data in a modulated data signal such as a carrier wave or other transport mechanism and includes any information delivery media.

Processor(s) 710 is further coupled via bus 705 to a display 750, such as a Liquid Crystal Display ("LCD"), for displaying information related to gas in the upper atmosphere and/or to a molecular beam. Depending on the location of the computing system 700, an input device 740, such as a keyboard, and a control device 745, such as a computer mouse, may be further coupled to bus 705 to enable a user to interface with computing system 700. However, in certain embodiments, such as those where computing system 700 is located on a space vehicle, a physical keyboard, mouse, and display may not be present. Any type and combination of input devices may be used as a matter of design choice. Given that the hardware components are on a vehicle, the interface devices may not exist in some embodiments, or may be located remotely to the vehicle, such as on Earth.

Memory 715 stores software modules that provide functionality when executed by processor(s) 710. The modules include an operating system 725 for system 700. The modules further include an upper atmosphere gas module 730 that is configured to determine the characteristics of the gas in the upper atmosphere when impinging on the windowless microbolometer array. System 700 may include one or more additional functional modules 735 that include additional functionality. For example, additional functional modules 735 may include molecular beam module configured to determine the characteristics of the molecular beam when impinging on the windowless microbolometer array.

One skilled in the art will appreciate that a "computing system" could be embodied as a computer, a server, a console, or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology, including cloud computing systems.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, RAM, tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

Figure 8:
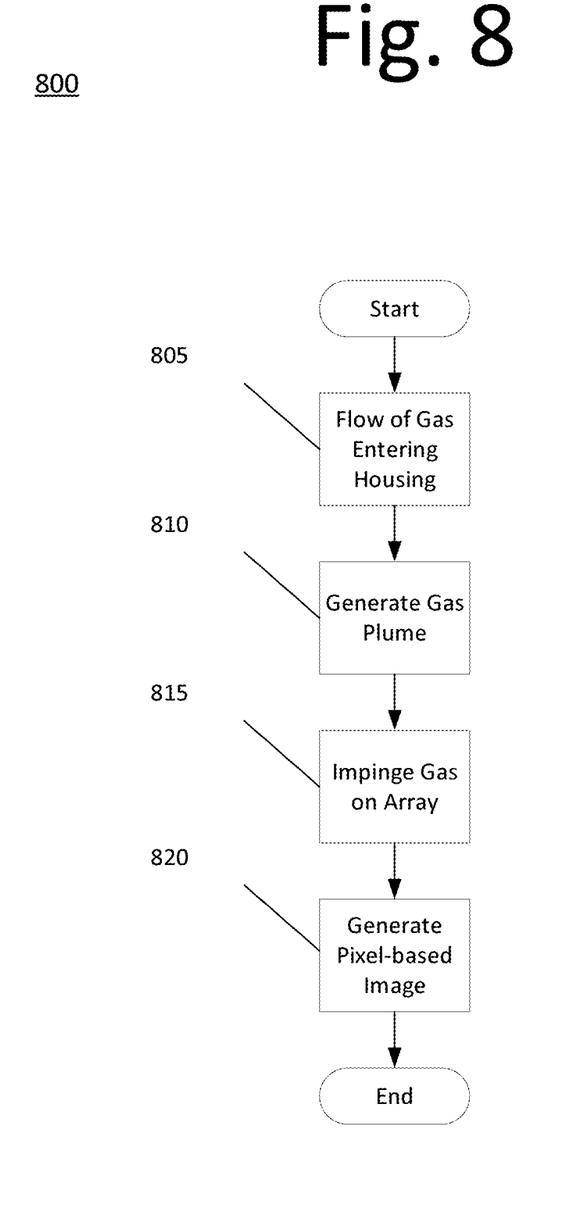
FIG. 8 is a flow diagram illustrating a process for measuring characteristics of gas in the upper atmosphere, according to an embodiment of the present invention.

FIG. 8 is a flow diagram 800 illustrating a process for measuring characteristics of gas in the upper atmosphere, according to an embodiment of the present invention. In this embodiment, the process begins at 805 with a flow of gas passing through an aperture of a housing and entering the housing. A plume of gas is created by the housing at 810, and the plume impinges on the windowless microbolometer array at 815. When the plume of gas impinges on the windowless microbolometer array, the computing system, as shown in FIG. 7, for example, may generate a pixel-based image of the impinged gas at 820. This pixel-based image may then provide information related to the characteristics of the gas in the upper atmosphere.

Figure 9:
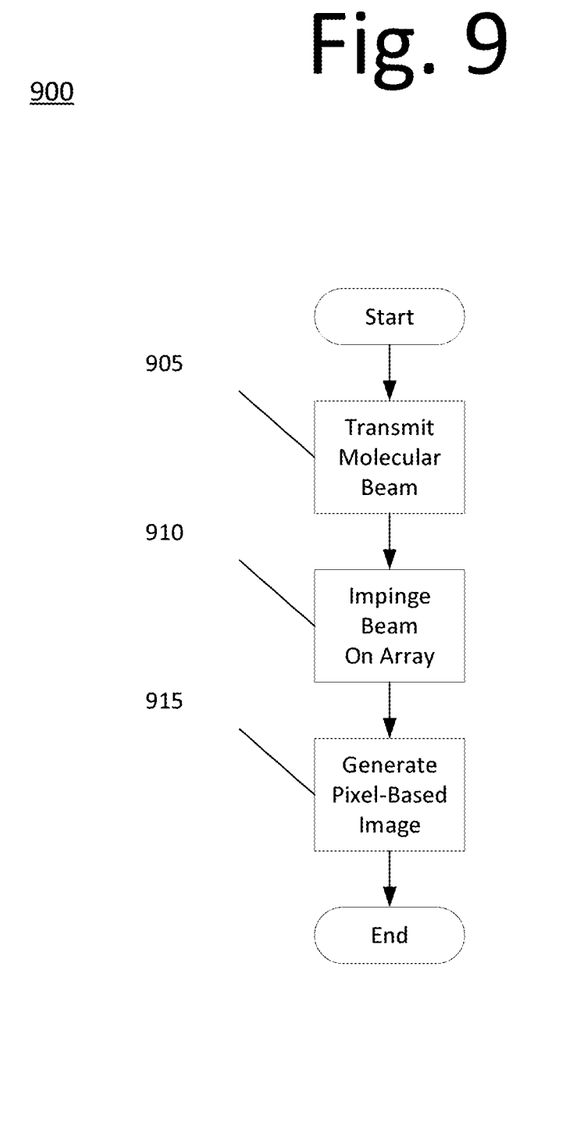
FIG. 9 is a flow diagram illustrating a process for measuring characteristics of a molecular beam, according to an embodiment of the present invention.

FIG. 9 is a flow diagram 900 illustrating a process for measuring characteristics of a molecular beam, according to an embodiment of the present invention. In this embodiment, the process begins at 905 with transmission of a molecular beam to a windowless microbolometer array. At 910, when the molecular beam impinges on the windowless microbolometer array, the computing system, as shown in FIG. 7, for example, may generate a pixel-based image of the impinged gas at 915. This pixel-based image may then provide information related to the characteristics of the molecular beam in the vacuum chamber.

It will be readily understood that the components of various embodiments of the present invention, as generally described and illustrated in the figures herein, may be arranged and designed in a wide variety of different configurations. Thus, the detailed description of the embodiments, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. An apparatus, comprising:
a windowless microbolometer array configured to interact with a flow of gas such that a pixel-based image of the gas is generated when the flow of gas impinges upon the windowless microbolometer arrays, wherein the interacting is with bulk of the gas.

2. The apparatus of claim 1, further comprising:
an aperture configured to admit the flow of gas at an angle into a housing.

3. The apparatus of claim 2, wherein the housing surrounds the windowless microbolometer array, and is configured to create a plume of gas that impinges upon the windowless microbolometer array.

4. The apparatus of claim 3, wherein the housing further comprises at least one hole on each side of the windowless microbolometer array, and is configured to allow gas to escape from the housing.

5. The apparatus of claim 1, further comprising:
a computing system configured to receive data from the windowless microbolometer array when the flow of gas impinges upon the windowless microbolometer array.

6. The apparatus of claim 5, wherein the computing system is configured to generate the pixel-based image of the gas to provide information related to density, temperature, and wind vector of the flow of gas.

7. The apparatus of claim 1, wherein the windowless microbolometer array is located in an upper atmosphere to measure density, temperature, and wind vector of the flow of gas.

8. The apparatus of claim 1, further comprising:
a chopper motor comprising at least one aperture configured to allow a flow of gas to flow through the at least one aperture and into an aperture of a housing.

9. The apparatus of claim 1, wherein the windowless microbolometer array is utilized in the upper atmosphere on a moving or stationary vehicle for insitu measurement of the bulk gas.

10. An apparatus, comprising:
an aperture configured to admit a flow of gas into a housing such that bulk of the gas impinges on a windowless microbolometer array; and
a computing system configured to generate a pixel-based image of the bulk gas that provides information related to density, temperature, and wind vector of the bulk gas when the bulk of the gas impinges upon the windowless microbolometer array.

11. The apparatus of claim 10, wherein the housing surrounds the windowless microbolometer array, and is configured to create a plume of gas that impinges on the windowless microbolometer array.

12. The apparatus of claim 10, wherein the housing further comprises at least two vents configured to allow gas to escape the housing.

13. The apparatus of claim 10, wherein the housing further comprises baffles configured to direct a majority of the gas to impinge upon the windowless microbolometer array.

14. The apparatus of claim 10, further comprising:
a chopper wheel comprising at least one aperture configured to allow the flow of gas to pass through the at least one aperture and into the aperture of the housing.

15. The apparatus of claim 14, further comprising:
a motor configured to rotate the chopper wheel such that the flow of gas is allowed to pass through the at least one aperture of the chopper wheel.

16. The apparatus of claim 10, wherein the windowless microbolometer array is utilized in the upper atmosphere on a moving or stationary vehicle for insitu measurement of the bulk gas.

17. An apparatus, comprising:
a windowless microbolometer array configured to interact with a molecular beam to provide information related to density, shape, and propagation of the molecular beam, wherein the interacting is of bulk molecular beam with the windowless microbolometer array.

18. The apparatus of claim 17, further comprising:
a computing system configured to generate a pattern when the molecular beam impinges upon the windowless microbolometer array, wherein
the pattern provides information related to the density, the shape, and the propagation of the molecular beam.

19. The apparatus of claim 17, wherein an amount of energy of the molecular beam deposited into each pixel of the windowless microbolometer array relates to an amount of energy in a gas particle impinging on a particular pixel.

20. The apparatus of claim 17, wherein the windowless microbolometer is located in a terrestrial vacuum or a space vacuum, allowing measurement of the molecular beam to be performed.

21. The apparatus of claim 17, further comprising:
a plurality of motors configured to move the windowless microbolometer array, rotate the windowless microbolometer array, or both, and the windowless microbolometer array allows the molecular beam to impinge on a wider area of, and from a direction on, the windowless microbolometer array.

22. The apparatus of claim 17, further comprising:
a set of apertures configured to be moved into and out of a field of view of the windowless microbolometer array to provide information as to direction, size, and cross-sectional shape of the molecular beam.

23. The apparatus of claim 17, wherein the windowless microbolometer array is within a vacuum chamber for measurement of the molecular beam.

* * * * *